United States Patent

Satake et al.

[19]

[11] Patent Number: 6,158,287
[45] Date of Patent: Dec. 12, 2000

[54] METHOD AND APPARATUS FOR MEASUREMENT OF DYNAMIC WATER BREAK RESISTANCE

[75] Inventors: Toshimi Satake; Yukiko Uehori, both of Tokyo, Japan

[73] Assignee: Nippon Paper Industries Co., Ltd., Japan

[21] Appl. No.: 09/175,350

[22] Filed: Oct. 20, 1998

[30] Foreign Application Priority Data

Oct. 24, 1997 [JP] Japan ..................................... 9-309541

[51] Int. Cl.⁷ ...................................................... G01N 3/08
[52] U.S. Cl. .............................................................. 73/835
[58] Field of Search ............................... 73/838, 827, 834, 73/835, 159, 828, 830; 162/49, 263

[56] References Cited

U.S. PATENT DOCUMENTS

| | | | |
|---|---|---|---|
| 2,893,241 | 7/1959 | Fisher et al. ................................ | 73/834 |
| 3,015,230 | 1/1962 | Obenshain ................................. | 73/834 |
| 4,970,250 | 11/1990 | Martinez et al. . | |
| 5,434,222 | 7/1995 | Reiners et al. . | |

*Primary Examiner*—Robert Raevis
*Attorney, Agent, or Firm*—Oblon, Spivak, McClelland, Maier & Neustadt, P.C.

[57] ABSTRACT

A novel method for measurement of dynamic water break resistance capable of predicting a degree of paper-cutting at the time of an offset printing and an apparatus for carrying out this method are provided. Both ends of a specimen paper having a size of short-side of from 3 to 15 mm and a long-side of from 120 to 320 mm are kept by a fixed chuck and a movable chuck positioned with a fixed spun length on a measurement table; from 1 to 30 $\mu$l of water is attached from a device unit for automatically attaching water onto a central portion of the specimen paper; after the attachment of water, a load is rapidly applied from the both ends of the specimen paper to measure a tensile strength of the specimen paper at the time of attachment of water; and a tensile strength of the specimen paper at the time of drying, i.e., in a state before the attachment of water, is also measured; and a dynamic water break resistance is displayed and evaluated from a percentage of the tensile strength of the specimen paper at the time of attachment of water to the tensile strength of the specimen paper at the time of drying.

3 Claims, 2 Drawing Sheets

METHOD AND APPARATUS FOR MEASUREMENT OF DYNAMIC WATER BREAK RESISTANCE

BACKGROUND OF THE INVENTION

1. Field of the Invention

The present invention relates to a novel method for measurement of dynamic water break resistance capable of predicting a degree of paper-breakage at the time of offset printing and to an apparatus for carrying out this novel method for measurement of dynamic water break resistance.

2. Description of the Related Art

Usually, a printing paper is required to have sizing properties to a some extent. Though this requirement to sizing properties is somewhat different depending on the nature required by a printing method employed, sizing has hitherto been to prevent a bleeding phenomenon of an ink when writing with a pen on paper. Accordingly, as a method of measurement for such sizing, one by which a degree of the bleeding phenomenon can be evaluated was sufficient, and it could be sufficiently achieved only by measuring the spreading of an ink on the surface of a paper layer or the penetration of the ink in the thickness direction.

As a method for measurement of the spreading of the ink on the paper surface, for example, there is known a carpentry sizing test method for electrically measuring the surface resistance of paper.

However, in rotary printing for subjecting a paper to continuous roll printing at a high speed and particularly, in a high-speed offset rotary printing in which a dampening water is used, the resistance to water absorption to a paper is important. This is because decrease in of the tensile strength of paper by water absorption results in paper-cutting. That is, in a method for measurement to represent a degree of bleeding phenomenon of an ink as in, for example, the conventional carpentry sizing test, it was difficult to precisely evaluate the water break resistance in the high-speed offset rotary printing.

A newspaper rotary press is a machine for undergoing high-speed printing using a roll paper, cutting and folding. Specifically, it is constituted from respective parts of (1) a paper-feeding part, (2) a printing part, (3) a color printing part, (4) a folding part, (5) a rail frame part, and (6) a driving part. In this newspaper rotary press, there is a sheet-run between the paper-feeding part and the printing part, between the printing part and the color printing part, and between the color printing part and the folding part, respectively. In this sheet-run, the tension of paper during running must be controlled. This is because if the tension is low, overlap, twist, or the like may likely occur, while if it is too high, wrinkling or paper-cutting may likely occur. In the case of newspaper rotary offset printing with an A-winding width, though in monochromatic printing, a tension of 40 kgf is usually applied, in color printing, a tension of from 70 to 80 kgf is applied in order to avoid the overlap. On the other hand, in the newspaper rotary offset printing, in order to control a loss in finish printing caused by blackening as low as possible, an excess of a dampening water is used at the time of start of the printing or of the replacement of a printing plate. Further, the dampening water retains in a space in a blanket joint, whereby the dampening water may attach onto a paper surface in a line to the width direction.

In this connection, it is considered that if an excess of water attaches onto a paper surface and penetrates into an interior of the paper layer, the tensile strength of the printing paper is lowered, thereby likely causing paper-cutting. For this reason, the sizing of paper, i.e., the resistance of water absorption, is required. In particular, in the case of color printing, the dampening water is brought into contact with the paper surface four times at one printing step. Accordingly, it is feared that even if a small amount of water attaches onto the paper surface, in case that the resistance to water absorption of paper is low, the water penetrates into an interior of the paper layer, whereby the tensile strength is markedly lowered. On the other hand, it is considered that in case where the resistance of water absorption is high, and the amount of water which penetrates into an interior of the paper layer is small, even if an excess of the dampening water attaches to the paper surface, the tensile strength is not lowered so much.

However, according to the conventional methods for measurement of sizing, in a sense of the counter measure for the paper-cutting, it was impossible to precisely grasp what extent of sizing (resistance to water absorption) is necessary for a paper to have high-speed offset printability. In other words, it was impossible to numerically express what extent of sizing (resistance to water absorption) is necessary for a printing paper which is desired for high-speed offset printing.

As a method for measuring both the sizing and strength of paper, there is a wet tensile strength test for measuring the tensile strength after immersing a paper in a distilled water as indicated in JIS P8135. This wet tensile strength test is one in which the whole of a paper specimen is immersed in a distilled water, whereby the tensile strength is measured in a completely wet state. However, this test is to be carried out under severe test conditions different from the water absorption state at the time of the actual offset rotary printing. Accordingly, it was impossible to apply this wet tensile strength test to products having a low sizing as in newspaper printing paper. Thus, in particular, it was impossible to quantitatively measure a degree at which the paper-cutting as actually generated by the attachment of an excess of the dampening water in the offset rotary printing occurs.

As described above, it is considered that in order to avoid a paper-cutting problem in the continuous offset rotary printing using a roll paper, previously grasping the physical properties of paper regarding the paper-breakage and in particular, controlling the resistance to water absorption of the paper is considered possible to avoid such trouble.

SUMMARY OF THE INVENTION

An object of the present invention is to provide a method for quantitative measurement of water break resistance at the time of offset rotary printing, i.e., resistance of paper-cutting (water break) by the attachment and transition of a dampening water at the time of printing, and an apparatus for carrying out this method.

The present inventors thought that the paper-cutting generated at the time of continuous offset rotary printing is caused by a decrease in the tensile strength of paper by the attachment of water in a state where a tension is applied to the paper.

Thus, the present inventors made extensive and intensive investigations with respect to a method for measurement of dynamic water break resistance in offset rotary printing, which comprises attachment of a proper amount of water onto a paper specimen and measurement of the tensile strength. As a result, the inventors have found a novel method for measurement of dynamic water break resistance capable of quantitatively measuring resistance of paper-cutting adapted for the actual state of the continuous offset rotary printing, by employing a method comprising attaching from 1 to 30 µl of water onto a central portion of a paper piece having a short-side of from 3 to 15 mm and a long-side of from 120 to 320 mm; immediately after the attachment of water, applying a load from both ends of the paper piece to measure a tensile strength at the time of the attachment of water; and measuring a tensile strength of the paper piece at the time of drying, i.e., in a state before the attachment of water, thereby evaluating dynamic water break resistance, i.e., a decrease rate of the strength at the time of attachment of water, from a percentage of the tensile strength at the time of attachment of water to the tensile strength at the time of drying. Also, the present inventors have found, as an apparatus for carrying out this method for measurement of dynamic water break resistance, an apparatus comprising a device unit for measuring a tensile strength; a device unit for automatically attaching a prescribed amount of water onto a central portion of a paper piece; and a unit for storing the tensile strength of the paper piece at the time of drying, i.e., in a state before the attachment of water, and the tensile strength of the paper piece at the time of the attachment of water as measured in the device unit for measuring a tensile strength, respectively and calculating dynamic water break resistance from a percentage of the tensile strength at the time of the attachment of water to the tensile strength at the time of drying, thereby displaying it.

DESCRIPTION OF THE PREFERRED EMBODIMENTS

Figure 1:
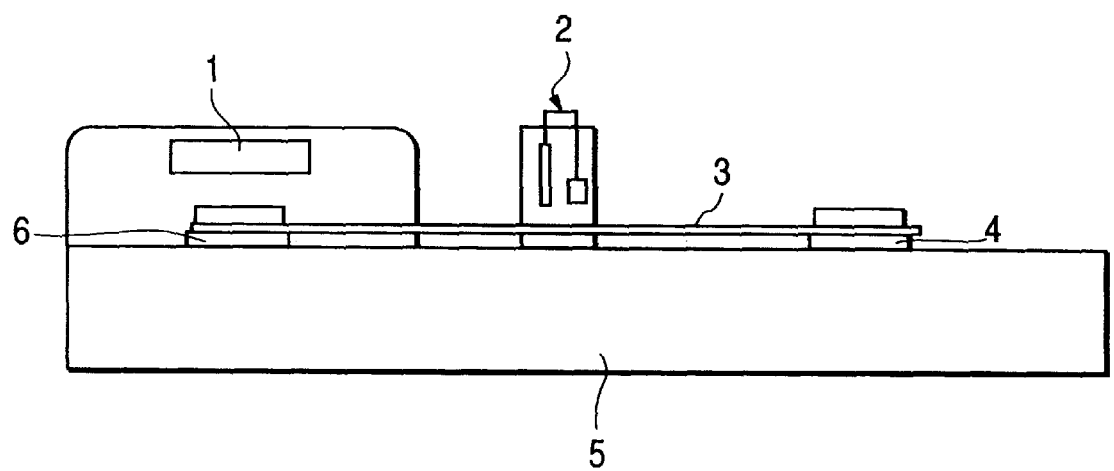
FIG. 1 is a drawing to explain one embodiment of an apparatus for measurement of dynamic water break resistance according to the present invention.

In continuous offset rotary printing using a paper, particularly an extra-light weight newsprint or a roll paper with a relatively low basis weight, the dynamic water break resistance as referred to in the present invention can be an index of resistance to penetration of water into a paper layer in case that an excess of dampening water is partially attached onto the paper during the printing.

In general, the strength of a paper is remarkably lowered in a water-containing state. By this property, the paper is readily disaggregated in water and hence, can be reused. From the viewpoint of recycle, it is not preferred to impart the sizing too much, thereby improving the wet strength more than required because the disaggregation properties of paper are lowered. That is, water break resistance so as to have proper disaggregation properties in a recycle step is preferable.

By the method for measurement of dynamic water break resistance according to the present invention, a wet strength can be made clear to an extent that no paper-cutting occurs at the time of continuous offset rotary printing while keeping proper disaggregation properties in a recycle step.

In the present invention, the paper specimen has a size of a short-side of from 3 to 15 mm and a long-side of from 120 to 320 mm. In particular, in the case that the attachment of water is carried out at one point, a size of a short-side of from 3 to 5 mm and a long-side of from 120 to 320 mm is preferred, and for the handling and the measurement apparatus of tensile strength, a size of a short-side of 5 mm and a long-side of from 120 to 180 mm is most preferred. Usually, in the case of mechanically-made paper, a paper specimen is prepared such that the flow direction (MD direction) at the time of paper-making is a long-side.

A proper amount of the attachment of water as referred to in the present invention is an amount close to the amount of the dampening water used in the actual offset printing. For the specimen paper having a size as described above, it is sufficient that water in an amount of 1 to 30 µl can be effectively attached. Further, as the method for the attachment of water, it is desired that the water to be attached does not give an impact to the paper surface as far as possible, and in case of manual attachment operations, a micropipette can be used. Water droplets can be mechanically and quantitatively dropped thereby achieving the attachment of water. Examples of means for mechanical and quantitative attachment of water include spontaneous dropping of water droplets, roll transition, and spraying from a fine nozzle or by an ink jet mode. More specifically, a device such as a dynamic contact angle meter can be used. Still further, the water can be attached at not only one point but also multipoints or in a strip-like form toward the short-side direction. In this case, it is necessary that the short-side of the specimen paper are widened. In case that the water is attached at one point, a preferred amount of water to be attached is from 1 to, 5 µl.

The tensile strength test as referred to in the present invention is based on the measurement method as described in JIS P8113 to be used for a usual tensile strength test.

The dynamic water break resistance as referred to in the present invention is evaluated in terms of a percentage of the tensile strength at the time of attachment of water to the tensile strength at the time of drying as described above and represented by the following equation:

$$A=(C/B)\times 100$$

wherein
A: Dynamic water break resistance (%)
B: Tensile strength at the time of drying
C: Tensile strength at the time of attachment of water The present invention relates to a novel method adapted for evaluation of a dynamic water break resistance under various conditions at the time of continuous offset rotary printing and to an apparatus for carrying out such method. That is, according to the present invention, a proper amount of water is attached onto a paper piece, a load is rapidly applied to the paper piece to measure a tensile strength, and a dynamic water break resistance is evaluated from a percentage of the thus measured tensile strength to a tensile strength of a paper piece at the time of drying (in a state before the attachment of water) as measured separately. In other words, when the water penetrates into an interior of the paper layer, the tensile strength of the paper piece is markedly lowered. Accordingly, if the penetration of water into the interior of the paper layer is controlled, the strength of the paper is kept, whereby the strength at the time of drying is kept. In accordance with the measurement method of the dynamic water break resistance according to the present invention, a relation of the water break (paper-cutting) at the time of offset rotary printing with the strength of the paper can be judged by means of a simple table test, whereby the resistance to dampening water in a state similar to that in the offset rotary printing can be measured.

The apparatus for measurement of dynamic water break resistance according to the present invention comprises a device unit for measuring a tensile strength, a device unit for automatically attaching water, and a unit for calculating a dynamic water break resistance from the tensile strength (calculation from the above-described equation) and displaying it. While the above-described three units can be connected with each other, in case that only the device for automatically attaching water is not actuated, a usual tensile strength can also be measured. When a specimen paper is set, a prescribed amount of water is attached thereonto by means of, e.g., dropping, transition, or spraying, and a tensile strength is rapidly measured and then compared with a tensile strength as measured in a state at the time of usual drying where no water is attached, whereby a dynamic water break resistance value can be displayed.

One example of such apparatus for measurement of dynamic water break resistance is illustrated in FIG. 1. In FIG. 1, 1 denotes a display part for displaying a maximum load (tensile strength at the time of attachment of water and a tensile strength at the time of drying) when a specimen paper 3 to be measured is broken and a dynamic water break resistance. 2 denotes a device unit for automatically attaching from 1 to 30 µl of a distilled water or dampening water onto the central portion of the specimen paper. In the embodiment as shown in FIG. 1, the device unit is constructed such that the tensile strength is measured in a state where the specimen paper 3 is kept horizontally and hence, a distilled water or dampening water is automatically dropped from the upper portion. However, in case that the tensile strength is measured in a state where the specimen paper 3 is kept vertically as in a usual tensile strength test apparatus, a distilled water or dampening water may be automatically attached by means of, e.g., transition or spraying from the side portion. 4 denotes a movable chuck for imparting a tension to the specimen paper 3 at a designated and prescribed tensile rate while keeping the end portion of the specimen paper 3 with a fixed span length, and in case that the data is previously inputted, a structure is preferred in which, when the end portion of the specimen paper 3 is kept, the device unit for automatically attaching water 2 is rapidly actuated in a connected manner, thereby attaching from 1 to 30 µl of a distilled water or dampening water onto a central portion of the specimen paper 3. The span length as referred to herein means a distance between the movable chuck 4 and a fixed chuck 6 as described later when the specimen paper 3 is fixed to the tensile strength measurement apparatus by the chucks 4 and 6, and the distance is preferably from 50 to 250 mm. Also, 5 denotes a measurement table, and 6 denotes a fixed chuck for fixing the other end portion of the specimen paper 3. By such apparatus, it is possible to not only measure the tensile strength of the specimen paper 3 at the time of drying but also rapidly measure the tensile strength of the specimen paper 3 after the attachment of water, thereby making the measurement of the dynamic water break resistance possible.

That is, the both ends of the specimen paper 3 as prepared are kept on the measurement table 5 by the fixed chuck 6 and the movable chuck 4 with a fixed span length; the movable chuck 4 is moved without actuating the device unit for automatically attaching water 2; a tension is imparted to the specimen paper 3 to measure a tension at which the specimen paper 3 is broken, i.e., a tensile strength of the specimen paper 3 at the time of drying; the device unit for automatically attaching water 2 is actuated to automatically attach a prescribed amount of distilled water or dampening water in a central portion of the specimen paper 3; the movable chuck 4 is rapidly moved; and a tension is imparted to the specimen paper 3 to measure a tension at which the specimen paper 3 is broken, i.e., a tensile strength of the specimen paper 3 at the time of attachment of water. Thus, a dynamic water break resistance is displayed in the display part 1.

The present invention is to provide a novel evaluation method adapted for various conditions at the time of continuous offset rotary printing and an apparatus for carrying out such method. In other words, a proper amount of water is attached on a paper piece, immediately thereafter, a load is applied to the paper piece, and a tensile strength is measured. When the water penetrates into an interior of the paper layer, the tensile strength of paper is markedly lowered. Accordingly, it is considered that if the penetration of water into an interior of the paper layer could be controlled, the strength of paper is kept, to thereby keep the strength of paper at the time of drying. According to the novel evaluation method and apparatus of the present invention, it is possible to judge a relation of the water break with the strength of paper at the time of continuous offset rotary-printing by means a simple table test. Namely, the dynamic water break resistance of paper in a state similar to that in offset rotary printing can be measured.

The present inventors have found a fact that even in samples having a similar spot water absorption, if the method for imparting sizing (on internal layer, external layer, or both thereof) is different, the dynamic water break resistance may be different. It is considered that this is because in case of external addition sizing, a barrier layer is formed on the paper surface, thereby preventing the penetration of water into an interior of the paper layer. Accordingly, it is considered that if a tension is applied at the time of printing to break the barrier layer on the paper surface, the water readily penetrates from a crack of the barrier layer into an interior of the paper layer having not subjected to sizing. In contrast, in case of internal layer sizing it is considered that since the sizing is subjected into an interior of the paper layer, even, when a tension is applied, it is difficult for water to penetrate into the interior of the paper layer. That is, it is considered that a difference in penetration properties of water into the interior of the paper layer in a state where a tension is applied controls the dynamic water break resistance of the paper. Thus, we cannot always say that if the spot water absorption is high, the resistance to paper-cutting at the time of offset rotary printing is also high. On the other hand, since the method for measurement of dynamic water break resistance according to the present invention enables to evaluate the penetration properties of water into an interior of the paper layer in a state that a tension is applied to the paper, it is considered that the spot water absorption correlates strongly with the paper-breakage at the time of offset rotary printing is high.

The present invention is described in more detail with reference to the following Examples. In each of the Examples and Comparative Examples, the method for measurement of dynamic water break resistance according to the present invention was carried out under, various conditions as described later by using the above-described apparatus for measurement of dynamic water break resistance of the present invention. In addition, the measurement of the spot water absorption, the wet tensile strength test of a conventional method, and the water break test by an offset rotary printing machine were carried out, if needed.

Dynamic Water Break Resistance

The same procedures as in JIS P8113 were followed, except that a prescribed amount of water was attached immediately before applying a load. Also, a tensile strength at the time of drying was measured according to JIS P8113, and a dynamic water break resistance was calculated from the tensile strength at the time of attachment of water and the tensile strength at the time of drying. Incidentally, the sample was prepared in such a manner that the MD direction was a long-side.

Spot Water Absorption

The same procedures as in Japan TAPPI No. 33 were followed. That is, 1 µl of a distilled water was softly dropped onto a sample as previously treated according to JIS P8111, and a time until the water completely penetrated into the paper layer was measured, a value of which was taken as a spot water absorption.

Wet Tensile Strength

The same procedures as in JIS P8135 were followed. After immersing a sample in a distilled water of 20±2° C. for 10 seconds, the sample was put on a 3-fold blotting paper, one blotting paper was covered thereon, the excess of water was removed by slightly pressing the sample, and a tensile strength was then rapidly measured according to JIS P8113 prior to any change in the water content of the sample.

Water Break Test

An offset rotary printing machine manufactured by Toshiba Corporation was used. A paper was run through a first drum and a second drum at 200 rpm, a tension (X) of a sheet-run till the first drum was fixed at 42 kgf, a tension (Y) from the second drum to an operation part was changed at every 5 kgf, and a tension at which the paper-cutting occurred was read. At this time, a print was supplied with a dampening water in the maximum amount of the dampening water-setting scale, and 30 seconds after the start of supply, a blanket was brought into contact with the running paper. A tension at the time of occurrence of paper-cutting was taken as a water break strength.

EXAMPLE 1

For seven kinds of newsprints having a different sizing (Samples A to G), the measurement of dynamic water break resistance and the water break test were carried out. The measurement of dynamic water break resistance was carried out under the conditions that the sample size was 15 mm in short-side and 250 mm in long-side, the spun length was 180 mm, the tensile rate was 10 mm/sec, and the amount of attachment of water was 5 µl. Incidentally, Sample A is a non-sized paper; Samples B and C are each an internal addition-sized paper having an internal layer-sizing agent added thereto in a wet end; Samples D to F are each an external layer-sized paper having an external layer-sizing agent coated thereon by a gate roll coater; and Sample G is a paper having subjected to a combination of internal layer-sizing and external addition-sizing.

Figure 2:
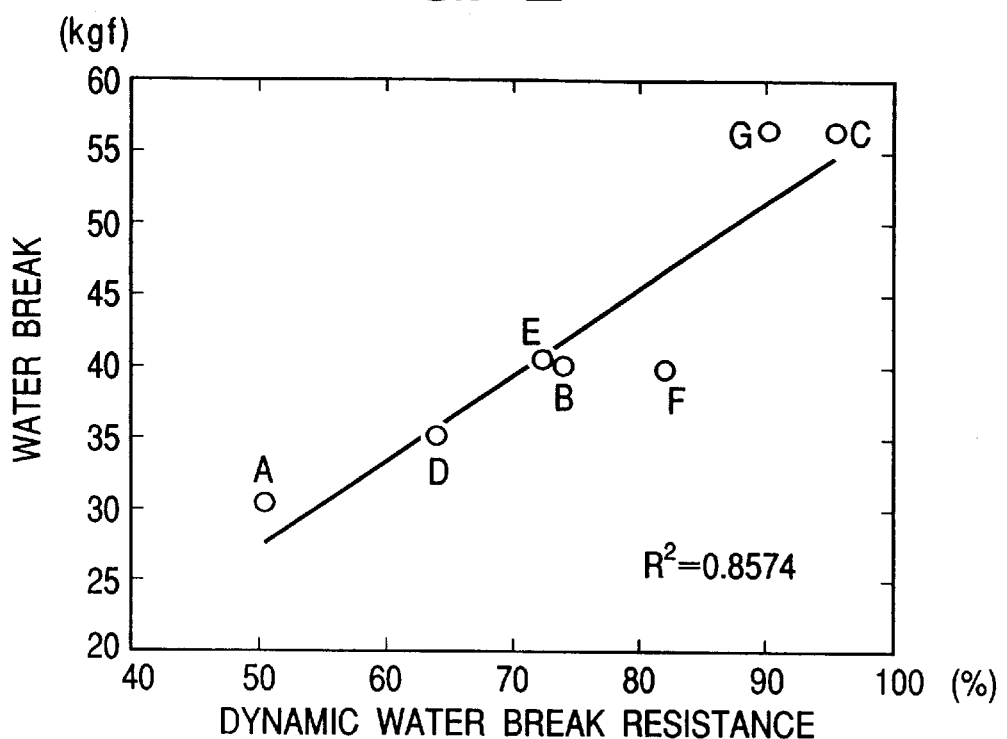
FIG. 2 is a graph to show a relation of the results (%) of dynamic water break resistance with the results (kgf) of water break in Example 1.

The results obtained are shown in Table 1 and FIG. 2. It can be understood that there is a high correlation between the dynamic water break resistance and the water break test.

COMPARATIVE EXAMPLE 1

Figure 3:
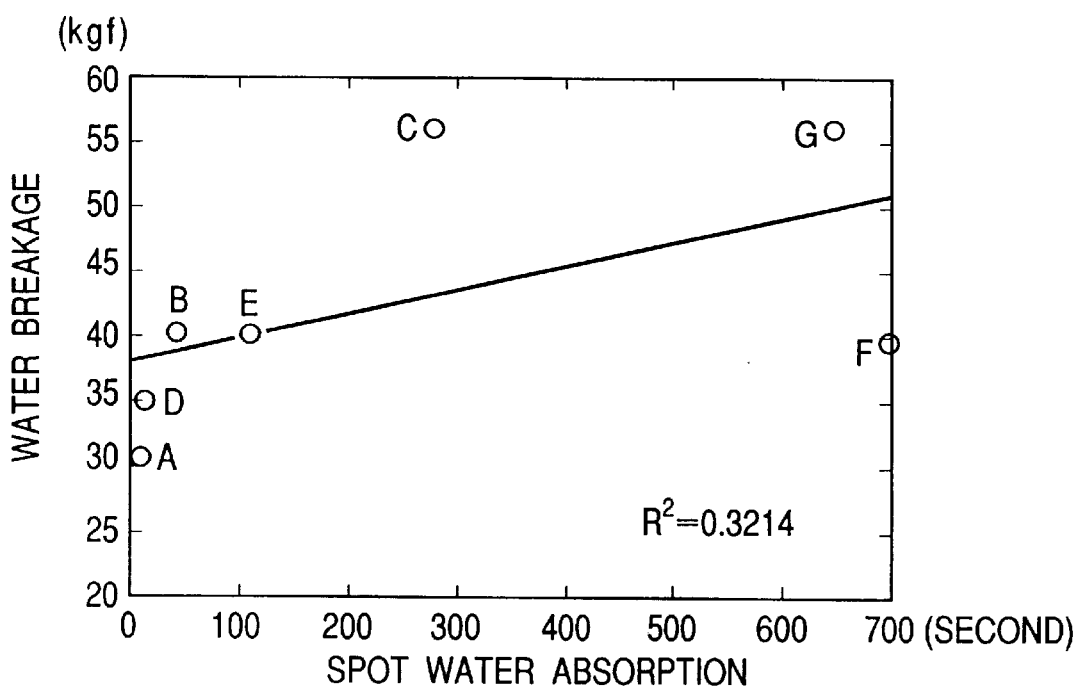
FIG. 3 is a graph to show a relation of the results (sec.) of spot water absorption with the results (kgf) of water break in Comparative Example 1.

With the samples as used in Example 1, the spot water absorption was measured. The results obtained are shown in Table 1 and FIG. 3 along with the results obtained in the water break test. It can be understood that there is no substantial correlation between the spot water absorption and the water break test.

TABLE 1

| Sample | Dynamic water break resistance (%) | Spot water absorption (sec) | Water break test (kgf) |
| --- | --- | --- | --- |
| A | 50.3 | 4 | 30.5 |
| B | 73.9 | 44 | 40.0 |
| C | 95.7 | 281 | 56.4 |
| D | 64.0 | 16 | 35.2 |
| E | 72.3 | 109 | 40.4 |
| F | 82.2 | 697 | 39.7 |
| G | 90.5 | 650 | 56.4 |

COMPARATIVE EXAMPLE 2

With the samples as used in Example 1, the wet tensile strength was measured. However, in the immersion in a distilled water for 10 seconds, the strength was so lowered that the wet tensile strength could not be measured.

In addition, while an attempt to shorten the immersion time was made, the scattering of the data was so high that no effective results were obtained in the measurement.

EXAMPLE 2

With newsprints having a different sizing, Sample H (a non-sized paper, spot water absorption: 4 seconds), Sample I (an internal layer-sized paper, spot water absorption: 42 seconds), and Sample J (a paper having subjected to a combination of internal layer-sizing and external layer-sizing, spot water absorption: 630 seconds), the dynamic water break resistance was measured in the same manner as in Example 1, except that the short-side length of the specimen paper was changed within a range of from 5 to 60 mm under the condition that the amount of attachment of water was 5 µl. The results obtained are shown in Table 2.

When the short-side length of the specimen paper exceeds 20 mm, a difference in the value of the dynamic water break resistance among the respective samples is small. It is considered that this is because, when the water is supplied to the specimen paper at one point, the short-side length of the specimen paper becomes long, and the area at which the water is attached in the short-side direction is relatively small, whereby it becomes difficult to judge a decrease in the tensile strength caused by the attachment of water.

TABLE 2

| Short-side length | Dynamic water break resistance (%) | | |
| --- | --- | --- | --- |
| (mm) | Sample H | Sample I | Sample J |
| 5 | 16.0 | 59.5 | 82.6 |
| 10 | 36.6 | 68.7 | 92.2 |
| 15 | 50.3 | 73.9 | 90.5 |
| 20 | 55.0 | 84.5 | 85.5 |
| 30 | 64.0 | 79.0 | 94.5 |
| 40 | 66.0 | 86.0 | 87.7 |
| 60 | 74.4 | 85.7 | 92.4 |

EXAMPLE 3

With the samples as used in Example 2, the dynamic water break resistance was measured in the same manner as in Example 1, except that the amount of the attachment of water was changed within a range of from 1 to 10 µl. The results obtained are shown in Table 3. While when the amount of water is 1 µl, a difference in the dynamic water break resistance among the respective samples is small, when the amount of water is from 3 to 10 µl, a distinct difference in the dynamic water break resistance among the respective samples appears.

TABLE 3

| Amount of water (µl) | Dynamic water break resistance (%) | | |
|---|---|---|---|
| | Sample H | Sample I | Sample J |
| 1 | 66.1 | 76.3 | 103.9 |
| 3 | 35.7 | 70.0 | 95.6 |
| 5 | 36.6 | 68.7 | 92.2 |
| 10 | 27.9 | 54.7 | 85.7 |

As have been described above in detail, it has hitherto been considered not possible to predict the degree of paper-cutting at the time of offset printing. On the other hand, according to the method for measurement of dynamic water break resistance of the present invention, so as to make a water absorption state adapted for the actual state of continuous offset rotary printing, water is attached onto a central portion of a paper piece having a size within a prescribed range; after the attachment of water, a load is rapidly applied from both ends of the paper piece; a tensile strength of the paper piece at the time of attachment of water is measured; and a tensile strength of the paper piece at the time of drying, i.e., in a state before the attachment of water, is also measured, whereby the dynamic water break resistance is evaluated from a percentage of the tensile strength at the time of attachment of water to the tensile strength at the time of drying. Thus, the present invention enables to predict the degree of paper-cutting at the time of offset printing.

In addition, according to the method of the present invention, it is possible not only to digitally express what degree of sizing (resistance to water absorption) is required for printing papers as desired for high-speed offset printing while they have proper disaggregation properties in order that they are readily disaggregated in water from the viewpoint of recycling, but also to evaluate the dynamic water break resistance with respect to products with a low sizing such as newsprints.

Furthermore, by carrying out the method according to the present invention to achieve the evaluation of the dynamic water break resistance, if a rate of reduction in strength at the time of attachment of water is 20% or less, it has been found that the paper-cutting hardly occurs with a usual tension.

And, since the apparatus for measurement of dynamic water break resistance according to the present invention is a simple structure comprising a device unit for measuring a tensile strength; a device unit for automatically attaching a prescribed amount of water onto a central portion of a paper piece; and a unit for storing the tensile strength of the paper piece at the time of drying, i.e., in a state before the attachment of water, and the tensile strength of the paper piece at the time of the attachment of water as measured in the device unit for measuring a tensile strength, respectively and calculating dynamic water break resistance from a percentage of the tensile strength at the time of the attachment of water to the tensile strength at the time of drying, thereby displaying it, the method for measurement of dynamic water break resistance according to the present invention, which is inexpensive and readily constructed and which has the above-described effects can be carried out.

In the light of the above, the present invention having various effects as described above will greatly contribute to not only the field of paper but also the field of offset rotary printing from the standpoint of industry.

While the invention has been described in detail and with reference to specific embodiments thereof, it will be apparent to one skilled in the art that various changes and modifications can be made therein without departing from the spirit and scope thereof.

What is claimed is:

1. A method for measurement of dynamic water break resistance, which comprises attaching from 1 to 30 µl of water onto a central portion of a paper piece having a short-side of from 3 to 15 mm and a long-side of from 120 to 320 mm; immediately after the attachment of water, applying a load from both ends of said paper piece to measure a tensile strength at the time of the attachment of water; and measuring a tensile strength of the paper piece at the time of drying, i.e., in a state before the attachment of water, thereby evaluating a dynamic water break resistance from a percentage of the tensile strength at the time of attachment of water to the tensile strength at the time of drying.

2. An apparatus for measurement of dynamic water break resistance, which comprises a device unit for measuring a tensile strength; a device unit for automatically attaching a prescribed amount of water onto only a central portion of a paper piece; and a unit for storing the tensile strength of the paper piece immediately after the time of drying, i.e., in a state before the attachment of water, and the tensile strength of the paper piece immediately after the time of the attachment of water as measured in said device unit for measuring a tensile strength, respectively and calculating dynamic water break resistance from a percentage of the tensile strength at the time of the attachment of water to the tensile strength at the time of drying, thereby displaying the dynamic water break resistance.

3. The apparatus according to claim 2, wherein:

the prescribed amount of water is from 1 to 30 µl; and the piece of paper has a short side of from 3 to 15 mm and a long side of from 120 to 320 mm.

* * * * *

UNITED STATES PATENT AND TRADEMARK OFFICE
CERTIFICATE OF CORRECTION

PATENT NO. : 6,158,287
DATED : December 12, 2000
INVENTOR(S): Toshimi Satake, et al.

It is certified that an error appears in the above-identified patent and that said Letters Patent is hereby corrected as shown below:

On the title page, Item [73], the Assignee's city of residence is omitted. Item [73] should read as follows:

[73] Assignee: Nippon Paper Industries Co., Ltd.,
Tokyo, Japan

Signed and Sealed this

First Day of May, 2001

Attest:

NICHOLAS P. GODICI

*Attesting Officer*       *Acting Director of the United States Patent and Trademark Office*